US008507705B2

(12) United States Patent
Zhang et al.

(10) Patent No.: US 8,507,705 B2
(45) Date of Patent: Aug. 13, 2013

(54) C2-SYMMETRICAL RUTHENOCENE DIPHOSPHINE LIGANDS ONLY WITH SURFACE CHIRALITY AND THEIR MANUFACTURE

(75) Inventors: Wanbin Zhang, Shanghai (CN); Fang Xie, Shanghai (CN); Delong Liu, Shanghai (CN); Li Luo, Shanghai (CN); Genghong Hua, Shanghai (CN); Jian Shang, Shanghai (CN)

(73) Assignee: Shanghai Jiaotong University, Shanghai (CN)

( * ) Notice: Subject to any disclaimer, the term of this patent is extended or adjusted under 35 U.S.C. 154(b) by 627 days.

(21) Appl. No.: 12/303,767

(22) PCT Filed: Jun. 8, 2007

(86) PCT No.: PCT/CN2007/001824
§ 371 (c)(1),
(2), (4) Date: Mar. 27, 2009

(87) PCT Pub. No.: WO2007/140717
PCT Pub. Date: Dec. 13, 2007

(65) Prior Publication Data
US 2011/0160474 A1      Jun. 30, 2011

(30) Foreign Application Priority Data

Jun. 8, 2006   (CN) .......................... 2006 1 0027408
Jun. 8, 2006   (CN) .......................... 2006 1 0027409

(51) Int. Cl.
*C07F 15/00*          (2006.01)
(52) U.S. Cl.
USPC ............................................. 556/16; 556/22
(58) Field of Classification Search
USPC ....................................... 556/13, 136, 16, 22
See application file for complete search history.

(56) References Cited

U.S. PATENT DOCUMENTS

| 5,760,264 A | 6/1998 | Brieden |
| 2006/0241315 A1 | 10/2006 | Spindler et al. |

FOREIGN PATENT DOCUMENTS

| CN | 1166835 A | 12/1997 |
| CN | 1876666 A | 12/2006 |
| CN | 1876667 A | 12/2006 |
| CN | 1876668 A | 12/2006 |
| JP | 2000-256384 A | 9/2000 |
| JP | 2005-47883 A | 2/2005 |
| WO | 2004/099226 A1 | 11/2004 |

OTHER PUBLICATIONS

Salter, R. et al., "2-nitroferrocenyloxazolines: precursors to nitrofulvalenes and derivatives of (pS)- and (pR)-2-aminoferrocenecarboxylic acids," Tetrahedron: Asymmetry, (1998) 9: 4239-4247.*

March, J. Advanced Organic Chemistry, Reactions, Mechanisms and Structure, 3rd ed. (1985) pp. 354, 1101.*
Zhang, W. et al. "Highly diasteroselective ortho-lithiation of 1,1'-bis(oxazolinyl)ferrocene directed to C2-symmetric chiral ligands," Tetrahedron: Asymmetry (1996) 7: 451-460.*
Zhang, W. et al. "Novel C2-symmetric diphosphine ligand with only the planar chirality of ferrocene," Tetrahedron Lett. (1996) 37: 7995-7998.*
Marquarding, D. et al. "Correlation of central and planar chirality in ferrocene derivatives," JACS (1970) 92: 5389-5393.*

(Continued)

*Primary Examiner* — Porfirio Nazario Gonzalez
(74) *Attorney, Agent, or Firm* — Westerman, Hattori, Daniels & Adrian, LLP

(57) ABSTRACT

The invention affords $C_2$-symmetrical ruthenocene diphosphine ligands with surface chirality and their manufacture. The present invention uses (S)-(S)-1,1'-2(diphenylphosphino)-2,2'-2[(S)-4-isopropyloxazolinyl] ruthenocene as raw material and the product is prepared through two or three steps of reaction. At the action of trifluoroacetic acid, (S)-(S)-1,1'-2(diphenylphosphino)-2,2'-2[(S)-4-isopropyloxazolinyl] ruthenocene first removes oxazoline and gets ester amides compound which then carries out ester exchange or reduction alkylation and gets the product of ruthenocene diphosphine ligand with surface chirality. The ligands prepared with the structure as follows from the invention can be used in all kinds of metallic catalysis asymmetric reaction and has good reaction activity and stereoselectivity, wherein R is methyl or ethyl, $R^1$ is linear or branched alkyl, cycloalkyl, alkoxy, aryl, aralkyl and alkyl amino.

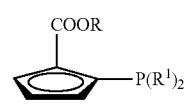

(1a)

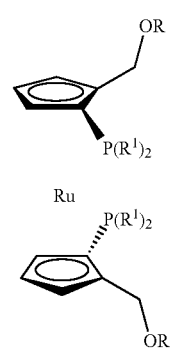

(1b)

10 Claims, No Drawings

(56) References Cited

OTHER PUBLICATIONS

Sutcliffe, O. et al. "Planar chiral 2-ferrocenyloxazolines and 1,1'-bis(oxazolinyl)ferrocenes—syntheses and applications in asymmetric catalysis," Tetrahedron: Asymmetry (2003) 14: 2297-2325.*

Park et al., Tetrahedron Letters, vol. 37, No. 34, pp. 6137-6140 (1996).*

International Search Report of PCT/CN2007/001824, date of mailing: Aug. 30, 2007.

* cited by examiner

C2-SYMMETRICAL RUTHENOCENE DIPHOSPHINE LIGANDS ONLY WITH SURFACE CHIRALITY AND THEIR MANUFACTURE

TECHNICAL FIELD

The present invention relates to a chiral ligand in the chemical industry field and its preparation method, more specifically, to a $C_2$-symmetrical ruthenocene diphosphine ligand having only planar chirality and its preparation method.

BACKGROUND

The rapid growth of chiral pharmaceutical industry benefits largely from the great development of asymmetric synthesis methodology which, in reverse, is facilitated by chiral pharmaceutical industry as well. Asymmetric catalytic organic synthesis is one of the most efficient and favorable ways to obtain chiral compounds. In asymmetric catalytic organic synthesis, the key point to achieve high reactivity and enantioselectivity is the structure of chiral phosphine ligands. Therefore, development of chiral phosphine ligands is always a research focus in both academic and industrial field.

In 1996, ZHANG Wanbin and IKEDA Isao et al. synthesized for the first time a $C_2$-symmetrical ferrocene-P,P-ligand having only planar chirality, and used it successfully in an allylic substitution reaction, achieving an optical yield as high as 94% e.e.

Just as in $C_2$-symmetrical axial chiral ligands, in the asymmetric catalytic reaction, the degree of the dihedral angle created by ligation between chiral ligands and metals tends to be the key factor influencing the asymmetric induction in a catalytic reaction. A slight change in such an angle could impact the stereoselectivity of the asymmetric catalytic reaction considerably. It could be expected that, for the ferrocene-based ligands, the distance between the two cyclopentadiene rings could be adjusted by changing the metallocene. Consequently, the dihedral angle (torsional angle) formed during ligation between the ligand and the metal would be changed, and eventually the chiral field in the asymmetric catalytic reaction could be changed. Following this idea, in the present invention, a novel $C_2$-symmetrical ruthenocene diphosphine ligand having only planar chirality is designed and synthesized so as to screen for novel universal catalysts with high catalytic activity and enantioselectivity by investigating the influence of the dihedral angle in planar chirality on the asymmetric catalytic effectiveness.

Through a literature research in the prior art, no subject matter same or similar as that of the present invention is found up to now.

SUMMARY OF THE INVENTION

To overcome the disadvantages in the prior art, the object of the present invention is to provide a $C_2$-symmetrical ruthenocene diphosphine ligand having only planar chirality so as to screen for planar chiral ligands with better asymmetric catalytic activity.

The present invention is carried out through the following technical solution. The $C_2$-symmetrical ruthenocene diphosphine ligand having only planar chirality as described herein has the following formula (1a) or (1b) as shown below.

(1a)

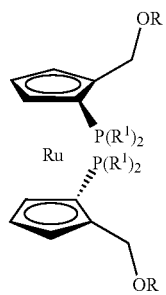

(1b)

Further, the planar chirality of ligands of the present invention is S,S configuration.

In addition, in the ruthenocene ligand having only planar chirality of the present invention, $R^1$ is phenyl.

Moreover, the present invention also provides a method for synthesizing a $C_2$-symmetrical ruthenocene diphosphine ligand having only planar chirality, characterized by, synthesizing a $C_2$-symmetrical ruthenocene diphosphine ligand having only planar chirality as shown in formula (1a),

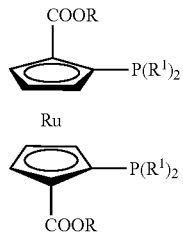

(1a)

In the formula (1a), R and $R^1$ are defined as above.

This synthesizing method includes:

Step (1): reacting a bisoxazoline compound as shown in formula (2) with an acid in a solvent to open the oxazoline ring, and then reacting the thus obtained compound with acetic anhydride to give the corresponding ester amide compound,

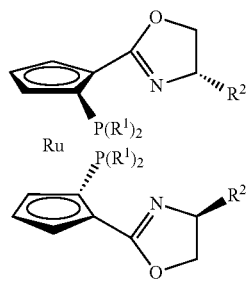

(2)

In the formula (2), $R^1$ is defined as above, and $R^2$ represents an alkyl group;

Step (2A): reacting the ester amide compound with an alkoxide as shown in the following formula:

R-OM wherein R is defined as above, and M represents an alkali metal atom.

Further, the present invention also provides a method for synthesizing a $C_2$-symmetrical ruthenocene diphosphine ligand having only planar chirality, characterized by, synthesizing a $C_2$-symmetrical ruthenocene diphosphine ligand having only planar chirality as shown in the following formula (1b),

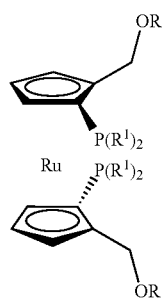

(1b)

In the formula (1b), R, $R^1$ are defined as above.

This synthesizing method includes:

Step (1): reacting a bisoxazoline compound as shown in the following formula (2) with an acid in a solvent to open the oxazoline ring, and then reacting the thus obtained compound with acetic anhydride to give the corresponding ester amide compound,

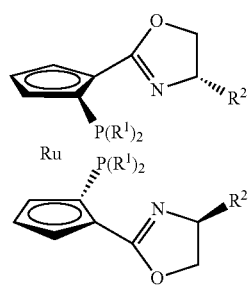

(2)

In the formula (2), $R^1$ is defined as above, and $R^2$ represents an alkyl group;

Step (2B): reacting the ester amide compound with a strong base, and reacting the thus obtained compound with an alkylating agent as shown in the following formula under a basic condition:

$R_2SO_4$ wherein R is defined as above.

Further, the present invention also provides a method for synthesizing a $C_2$-symmetrical ruthenocene diphosphine ligand having only planar chirality, characterized in that, in the step (1) described above, the acid is trifluoroacetic acid.

Further, the present invention provides a method for synthesizing a $C_2$-symmetrical ruthenocene diphosphine ligand having only planar chirality, characterized in that, in the step (1) described above, a hydrolyzation is conducted at the presence of trifluoroacetic acid, and the afforded hydrolysis product is reacted with acetic anhydride under a basic condition for acylation.

Further, the present invention provides a method for preparing a $C_2$-symmetrical ruthenocene diphosphine ligand having only planar chirality, characterized in that, in the step (2B) described above, the strong base is lithium aluminum tetrahydride.

The ligand of the present invention is a $C_2$-symmetrical diphosphine ligand having only planar chirality. Such a ligand can be used in various metal-catalytic asymmetric reactions, for instance, asymmetric cyclopropanation, allylic substitution, hydrogenation of functionalized or unfunctionalized alkenes and imines or the like, with high reactivity and stereoselectivity, and has a great potential of application.

Furthermore, the ligand synthesized according to the present invention is a novel $C_2$-symmetrical ruthenocene-based diphosphine ligand having only planar chirality. Further, the principle between the ligand structure-activity relationship and efficacy of asymmetric catalysis can be found, and based thereon the novel universal catalysts with high catalytic activity and enantioselectivity could be designed and synthesized.

EMBODIMENTS OF THE INVENTION

The $C_2$-symmetrical ruthenocene diphosphine ligand having only planar chirality of the present invention has the formula (1a) or (1b) as shown below.

(1a)

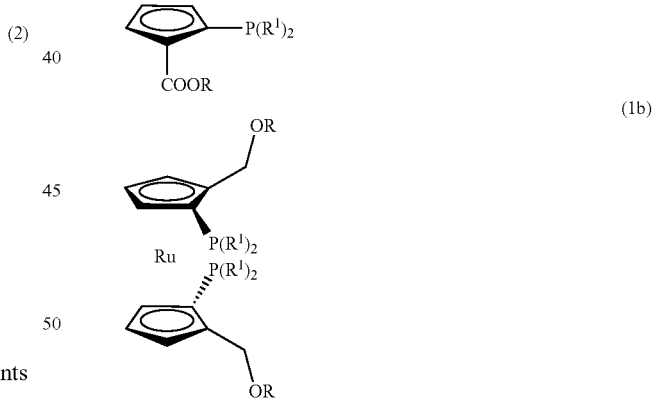

(1b)

In the formula (1a) or (1b), R represents a methyl or ethyl, and $R^1$ represents a linear or branched alkyl, cycloalkyl, alkoxy, aryl, aralkyl. The linear or branched alkyl groups described above could be exemplified as linear or branched alkyl groups having the carbon number of 1~18, such as methyl, ethyl, n-propyl, isobutyl, t-butyl, n-hexyl, isohexyl, n-heptyl, n-octyl, isooctyl, n-decyl, n-octadecyl, isooctadecyl and the like. Among those alkyl groups, linear or branched alkyl groups having the carbon number of 1~5 are preferred. The cycloalkyl groups described above could be exemplified as cyclopentyl, cyclohexyl and the like. The aryl groups described above could be exemplified as phenyl, tolyl, xylyl, naphthyl and the like. The aralkyl groups described above could be exemplified as benzyl, phenylethyl and the like. Among those groups, especially preferably, the $R^1$ in the formula is a phenyl group.

To obtain the $C_2$-symmetrical ruthenocene diphosphine ligand having only planar chirality as shown above in formula (1a) or (1b), step (1) is firstly carried out according to reaction scheme (1) as below, i.e., after the bisoxazoline compound as shown in formula (2) is reacted with an acid in the solvent to open the oxazoline ring (abbreviated as "reaction 1-1" thereafter), the obtained compound is reacted with acetic anhydride (abbreviated as "reaction 1-2" thereafter), to give the corresponding ester amide compound (as shown in formula (3)). Thereafter, step (2A) or (2B) is carried out as described below.

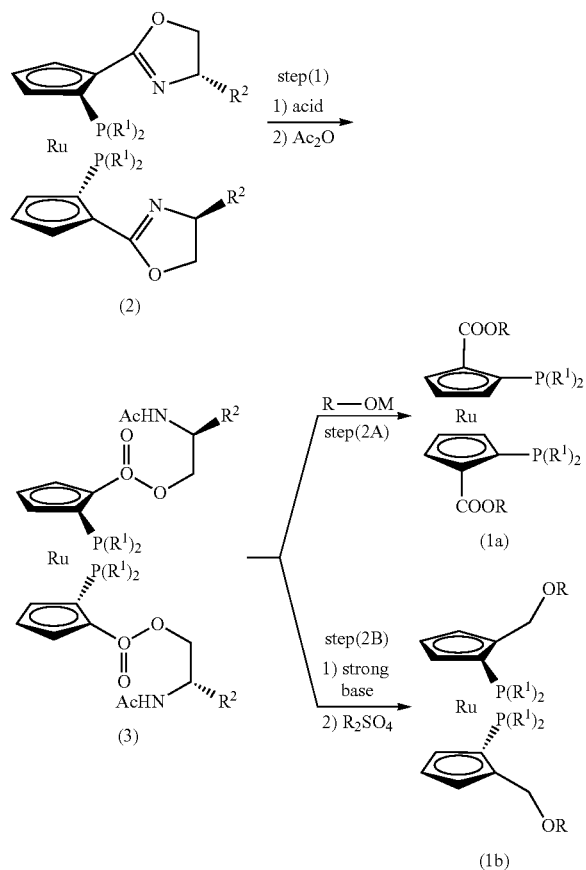

wherein R, $R^1$, $R^2$ and M are defined as above.

In the formula (2) of the bisoxazoline compound used in step (1) as starting material, R is defined as above. $R^2$ represents an alkyl group, and the alkyl species are not particularly limited. For example, preferred is a lower alkyl group having the carbon number of 1~5, such as methyl, ethyl, propyl or the like.

The acid used in reaction 1-1 could be exemplified as hydrochloric acid, sulfuric acid, oxalic acid, phosphoric acid, perchloric acid, periodic acid, hydrofluoric acid, methane sulfonic acid, p-toluene sulfonic acid, benzene sulfonic acid, trifluoroacetic acid, glacial acetic acid or the like. Those acids can be used alone, or can be used in combination of two or more. Among those, trifluoroacetic acid is specifically preferred. The acid is used in an amount of 1~50 molar equivalence, and preferably 15~35 molar equivalence, in relation to the mole number of the bisoxazoline compound as shown in formula (2). Moreover, the solvent used could be exemplified as water, lower alkyl halide, aromatic hydrocarbons, di(lower alkyl)ethers, cyclic ethers, di(lower alkoxy)ethane, aliphatic amides or the like. Those solvents can be used alone, or can be used in combination of two or more as a mixed solvent. The organic solvents could be exemplified as lower alkyl halides, such as chloroform, dichloromethane, dichloroethane, carbon tetrachloride or the like, aromatic hydrocarbons, such as benzene, chlorobenzene or the like, di(lower alkyl)ethers, such as diethyl ether, dimethyl ether or the like, cyclic ethers, such as tetrahydrofuran, dioxane or the like, di(lower alkoxy) ethanes, such as, 1,2-dimethoxy ethane, 1,2-diethoxy ethane, 1,2-dibutoxy ethane, 1,2-dibenzyloxy ethane or the like, and aliphatic amides, such as, dimethyl formamide and the like. In the present invention, the solvent used in reaction 1-1 is preferably a mixed solvent of water and tetrahydrofuran.

In the reaction 1-1, the ring-opening reaction of bisoxazoline compounds is carried out under the following condition. The reaction temperature is lower than 40° C., and preferably −20~30° C., and the reaction time is more than 5 hours, and preferably 10~30 hours.

In the step (1), the reaction 1-2 is carried out after completion of the reaction 1-1 described above, i.e., the compound obtained by the ring-opening reaction of the bisoxazoline compound is reacted with acetic anhydride in a solvent.

The acetic anhydride is added in an amount of 2~50 molar equivalence, and preferably 30~40 molar equivalence, in relation to the mole number of the bisoxazoline compound as shown in the above formula (2). Moreover, the solvent used in the reaction 1-2 could be exemplified as lower alkyl halide, aromatic hydrocarbons, di(lower alkyl)ethers, cyclic ethers, di(lower alkoxy)ethane, aliphatic amides or the like. Those solvents can be used alone, or can be used in combination of two or more as a mixed solvent. Specifically, the solvents could be exemplified as lower alkyl halides, such as chloroform, dichloromethane, dichloroethane, carbon tetrachloride or the like, aromatic hydrocarbons, such as benzene, chlorobenzene or the like, di(lower alkyl)ethers, such as diethyl ether, dimethyl ether or the like, cyclic ethers, such as tetrahydrofuran, dioxane or the like, di(lower alkoxy)ethanes, such as, 1,2-dimethoxy ethane, 1,2-diethoxy ethane, 1,2-dibutoxy ethane, 1,2-dibenzyloxy ethane or the like, and aliphatic amides, such as, dimethyl formamide and the like. Those solvents can be used alone, or be used in combination of two or more. Furthermore, for the reaction described above, the reaction efficiency could be improved by conducting the reaction under a basic condition. The bases that can be used could be exemplified as inorganic bases, such as, sodium hydroxide, sodium carbonate, sodium bicarbonate, potassium hydroxide, potassium carbonate, potassium bicarbonate, calcium hydroxide, calcium carbonate, barium hydroxide, ammonia or the like, organic bases, such as, trimethylamine, N,N-dimethyl cyclohexylamine, N,N-diethyl cyclohexylamine, N,N-dimethyl benzylamine, N,N'-dimethyl piperazine, N,N-dimethyl aniline, N,N-diethyl aniline, N,N,N',N'-tetramethyl-1,3-propylene diamine, pyridine, α-methylpyridine, β-methylpyridine, γ-methylpyridine, 4-ethyl morpholine, triethylenediamine, 1,3-diazabicyclo[5,4,0]undecene, 1,8-diazabicyclo[5,4,0]undec-7-ene, N-ethyl piperidine, quinoline, isoquinoline, N,N-dimethyl piperazine, N,N-diethyl piperazine, quinaldine, 2-ethyl pyridine, 4-ethyl pyridine, 3,5-dimethylpyridine, 2,6-dimethylpyridine, 4-methyl morpholine, 2,4,6-trimethylpyridine or the like, and ion exchange resins having pyridyl or dimethylamino benzyl groups, or the like. Among those bases, pyridine is particularly preferred. The base can be added in an amount of 10~100 molar equivalence, and preferably 35~65 molar equivalence, in relation to the mole number of the bisoxazoline compound as shown in the above formula (2).

The reaction condition for the reaction 1-2 is as following: the reaction temperature is −10~50° C., and preferably 10~35° C., and the reaction time is more than 5 hours, and preferably 10~30 hours.

After completion of the reaction, the target resultant is recovered after removing the solvent to afford the ester amide compound (as shown in formula (3)).

In the present invention, by conducting the step (2A) or (2B) with the ester amide compound obtained in the step (1) as described above, the target product, i.e., the $C_2$-symmetrical ruthenocene diphosphine ligands having only planar chirality as shown in formula (1a) or (1b) is thus obtained.

In step (2A), the ester amide compound (formula (3)) obtained in step (1) is reacted with the alkoxide as shown in the formula below in a solvent,

R-OM (wherein R is defined as above, and M represents an alkali metal.)

to affording the $C_2$-symmetrical ruthenocene diphosphine ligand having only planar chirality as shown in formula (1a) below,

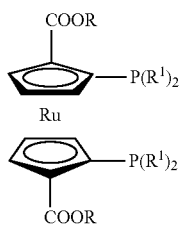

(1a)

In formula (1a), R and $R^1$ are defined as above.

The alkoxide used in step (2A) is shown in the following formula:

R-OM wherein R is defined the same as the R in formula (1a). Particularly, as described above, R is a methyl or ethyl group. Further, M represents an alkali metal atom, such as, sodium, potassium or the like.

The alkoxide can be added in an amount of 10~100 molar equivalence, and preferably 30~50 molar equivalence, in relation to the mole number of the ester amide compound (as shown in formula (3)) obtained in step (1).

Moreover, the solvent that can be used could be exemplified as lower alkyl halide, aromatic hydrocarbons, di(lower alkyl)ethers, cyclic ethers, di(lower alkoxy)ethane, aliphatic amides or the like. Those solvents can be used alone, or can be used in combination of two or more as a mixed solvent. Particularly, the solvent could be exemplified as lower alkyl halides, such as chloroform, dichloromethane, dichloroethane, carbon tetrachloride or the like, aromatic hydrocarbons, such as benzene, chlorobenzene or the like, di(lower alkyl) ethers, such as diethyl ether, dimethyl ether or the like, cyclic ethers, such as tetrahydrofuran, dioxane or the like, di(lower alkoxy)ethanes, such as 1,2-dimethoxy ethane, 1,2-diethoxy ethane, 1,2-dibutoxy ethane, 1,2-dibenzyloxy ethane or the like, and aliphatic amides, such as dimethyl formamide and the like. Those solvents can be used alone, or can be used in combination of two or more.

The reaction condition is as follows: the reaction temperature is −10~100° C., and preferably 5~30° C., and the reaction time is more than 5 hours, and preferably 12~24 hours.

In step (2B), the ester amide compound (formula (3)) obtained in step (1) as described above is reacted with a strong base, and the obtained compound is then reacted with an alkylating agent as shown in the formula as below: $R_2SO_4$ (wherein R is defined as above) under a basic condition, to afford the $C_2$-symmetrical ruthenocene diphosphine ligand having only planar chirality as shown in formula (1b),

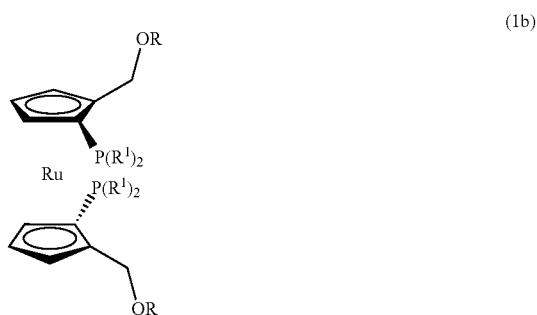

In formula (1b), R and $R^1$ are defined as above.

In step (2B), firstly, the ester amide compounds (formula (3)) obtained in step (1) as described above is reacted with a strong base in the solvent. The strong base that can be used could be exemplified as metal of sodium, metal of potassium, alkyl lithium, lithium aluminum tetrahydride, and the like. Among those strong bases, lithium aluminum tetrahydride is specially preferred. The strong base can be added in an amount of 1~20 molar equivalence, and preferably 3~10 molar equivalence, in relation to the mole number of the ester amide compound (formula (3)) obtained in the step (1). The solvent that can be used could be exemplified as lower alkyl halide, aromatic hydrocarbons, di(lower alkyl)ethers, cyclic ethers, di(lower alkoxy)ethane, aliphatic amides or the like. Those solvents can be used alone, or can be used in combination of two or more as a mixed solvent. Specifically, the solvents could be exemplified as lower alkyl halides, such as chloroform, dichloromethane, dichloroethane, carbon tetrachloride or the like, aromatic hydrocarbons, such as benzene, chlorobenzene or the like, di(lower alkyl)ethers, such as diethyl ether, dimethyl ether or the like, cyclic ethers, such as tetrahydrofuran, dioxane or the like, di(lower alkoxy)ethanes, such as, 1,2-dimethoxy ethane, 1,2-diethoxy ethane, 1,2-dibutoxy ethane, 1,2-dibenzyloxy ethane or the like, and aliphatic amides, such as, dimethyl formamide and the like. Those solvents can be used alone, or be used in combination of two or more.

The reaction condition is as follows. The reaction temperature is −10~100° C., and preferably 5~30° C. preferable, and the reaction time is more than 1 hour, and preferably 1~8 hours.

Next, in step (2B), the resultant (abbreviated as resultant ($2b_1$) thereafter) obtained above is reacted with an alkylating agent in the solvent.

As the alkylating agent, the alkyl sulfate ester as shown in the formula of $R_2SO_4$ (wherein R is defined as above) can be used, wherein R is equivalent to the R in formula (1b) as above. Particularly, as described above, R represents a methyl or ethyl group.

The alkylating agent can be added in an amount of 1~6 molar equivalence, and preferably 2~4 molar equivalence, in relation to the mole number of the above resultant ($2b_1$).

The bases could be exemplified as inorganic bases, such as, sodium hydroxide, sodium carbonate, sodium bicarbonate, potassium hydroxide, potassium carbonate, potassium bicarbonate, calcium hydroxide, calcium carbonate, barium hydroxide, ammonia or the like, organic bases, such as, triethylamine, N,N-dimethyl cyclohexylamine, N,N-diethyl cyclohexylamine, N,N-dimethyl benzylamine, N,N'-dimethyl piperazine, N,N-dimethyl aniline, N,N-diethyl aniline, N,N,N',N'-tetramethyl-1,3-propylene diamine, pyridine, α-methyl pyridine, β-methylpyridine, γ-methylpyridine, 4-ethyl morpholine, triethylenediamine, 1,3-diazabicyclo[5,4,0]undec ene, 1,8-diazabicyclo[5,4,0]undec-7-ene, N-ethyl piperidine, quinoline, isoquinoline, N,N-dimethyl piperazine, N,N-diethyl piperazine, quinaldine, 2-ethyl pyridine, 4-ethyl pyridine, 3,5-dimethylpyridine, 2,6-dimethylpyridine, 4-methyl morpholine, 2,4,6-trimethylpyridine or the like, and ion exchange resins having pyridyl or dimethylamino benzyl groups, or the like. Among those bases, sodium hydroxide is particularly preferred. The base can be added in an amount of 1~10 molar equivalence, and preferably 5~8 molar equivalence, in relation to the mole number of the above resultant ($2b_1$).

The solvents that can be used are solvents inert to the resultant, which could be exemplified as aprotic organic solvents, such as, N-methyl-2-pyrrolidone, propylene carbonate, ethylene carbonate, butylene carbonate, dimethyl carbonate, diethyl carbonate, γ-butyrolactone, 1,2-dimethoxyethane, tetrahydrofuran, 2-methyl tetrahydrofuran, dimethyl sulfoxide, 1,3-dioxolane, formamide, dimethyl formamide, dioxolane, acetonitrile, nitromethane, methyl formate, ethyl formate, trialkyl phosphate, trimethoxy methane, dioxolane derivatives, sulfolane, 3-methyl-2-oxazolone, propylene carbonate derivatives, tetrahydrofuran derivatives, diethyl ester, 1,3-propane sultone, methyl propionate, ethyl propionate or the like. Those solvent can be used alone, or be used in combination of two or more.

The reaction condition is as follow. The reaction temperature is –10~100° C., and preferably 20~50° C., and the reaction time is more than 5 hours, and preferably 8~48 hours.

In the above step (2A) or (2B) as above, after completion of the reaction, purification is carried out, if necessary, to afford the $C_2$-symmetrical ruthenocene diphosphine ligand having only planar chirality as shown in formula (1a) or (1b).

Example 1

The following examples are intended to explain the present invention. However, the present invention is not limited to those examples.

1. Preparation of Amide Ester (3)

(S)-(S)-1,1'-bis(diphenylphosphino)-2,2'-bis[(S)-4-isopropyloxazolinyl]ruthenocen e (1.65 g, 2 mmol) is dissolved in tetrahydrofuran (40 mL), into which water (2 mL), trifluoroacetic acid (3.8 mL, 49.4 mmol), and anhydrous sodium sulfate $Na_2SO_4$ (18.8 g) are then added successively. The suspension is stirred overnight at the room temperature, followed by filtration and removal of the solvent. The residue is dissolved in dichloromethane (40 mL), into which pyridine (7.2 mL, 89 mmol) and acetic anhydride (12.0 mL, 76.4 mmol) are added successively. After stirring overnight at room temperature, the mixture is diluted with dichloromethane (80 mL), and then washed with dilute hydrochloric acid (10%), water and saturated aqueous sodium chloride, and dried with anhydrous magnesium sulfate. After removal of the solvent, the residue is purified by column chromatography (ethyl acetate) to afford 1.56 g of the target product, y=82.8%.

$^1$H NMR (400 MHz, $CDCl_3$): δ7.34-7.14 (m, 20H, ArH), 6.59-6.58 (brs, 2H, NH), 5.39 (brs, 2H, RcH), 4.83 (brs, 2H, RcH), 4.39-4.34 (dd, J=4 Hz, 15.6, 2H, OCH), 4.05-4.01 (dd, J=3.6 Hz, 11.2 Hz, 2H, OCH), 3.90 (m, 2H, NCH), 3.82 (brs, 2H, FCH), 2.18-2.17 (m, 2H, $Me_2CH$), 2.16 (s, 6H, $COCH_3$), 1.02-1.00 (d, J=8.8 Hz, 6H, $CH_3$), 0.99-0.97 (d, J=8.8 Hz, 6H, $CH_3$).

2. Preparation of (S)-(S)-1,1'-bis(diphenylphosphino)-2,2'-bis(methoxycarbonyl) ruthenocene (1)

Amide ester (0.30 g, 0.32 mmol) is dissolved in tetrahydrofuran (8 mL), into which a sodium methoxide solution made with sodium (0.3 g, 40 equiv.) and methanol (10 mL) is added at room temperature, and then is stirred overnight at room temperature. The pH is adjusted to be neutral with 25% (v/v) acetic acid solution in methanol. The solvent is removed, and the residue is dissolved in dichloromethane (20 mL). The resultant is washed with water and saturated aqueous sodium chloride, and then dried with anhydrous magnesium sulfate. After removal of the solvent, the residue is purified by column chromatography (ethyl acetate/petroleum ether=1:6), to afford 0.17 g of pale green solid, y=71.5%.

$^1$H NMR (400 MHz, $CDCl_3$): δ7.34-7.17 (m, 20H, ArH), 5.42-5.41 (brs, 2H, FcH), 4.70-4.67 (t, J=5.2 Hz, 2H, FcH), 3.87 (brs, 2H, FcH), 3.70 (s, 6H, $OCH_3$).

Example 2

1. Preparation of Amide Ester (3)

(S)-(S)-1,1'-bis(diphenylphosphino)-2,2'-bis[(S)-4-isopropyloxazolinyl]ruthenocene (1.65 g, 2 mmol) is dissolved in tetrahydrofuran (40 mL), into which water (2 mL), trifluoroacetic acid (3.8 mL, 49.4 mmol), and anhydrous sodium sulfate $Na_2SO_4$ (18.8 g) are then added successively. The suspension is stirred overnight at the room temperature, followed by filtration and removal of the solvent. The residue is dissolved in dichloromethane (40 mL), into which pyridine (7.2 mL, 89 mmol) and acetic anhydride (12.0 mL, 76.4 mmol) are added successively. After stirring overnight at room temperature, the mixture is diluted with dichloromethane (80 mL), and then washed with dilute hydrochloric acid (10%), water and saturated aqueous sodium chloride, and dried with anhydrous magnesium sulfate. After removal of the solvent, the residue is purified by column chromatography (ethyl acetate) to afford 1.56 g of the target product, y=82.8%.

$^1$H NMR (400 MHz, $CDCl_3$): δ7.34-7.14 (m, 20H, ArH), 6.59-6.58 (brs, 2H, NH), 5.39 (brs, 2H, RcH), 4.83 (brs, 2H, RcH), 4.39-4.34 (dd, J=4 Hz, 15.6, 2H, OCH), 4.05-4.01 (dd, J=3.6 Hz, 11.2 Hz, 2H, OCH), 3.90 (m, 2H, NCH), 3.82 (brs, 2H, FCH), 2.18-2.17 (m, 2H, $Me_2CH$), 2.16 (s, 6H, $COCH_3$), 1.02-1.00 (d, J=8.8 Hz, 6H, $CH_3$), 0.99-0.97 (d, J=8.8 Hz, 6H, $CH_3$).

2. Preparation of (S)-(S)-1,1'-bis(diphenylphosphino)-2,2'-bis(ethoxycarbonyl) ruthenocene (1)

Amide ester (0.335 g, 0.36 mmol) is dissolved in tetrahydrofuran (20 mL), into which a sodium methoxide solution made with sodium (0.6 g, 70 equiv.) and ethanol (40 mL) is added at room temperature, and then is stirred overnight at room temperature. The pH is adjusted to be neutral with 25% (v/v) acetic acid solution in methanol. The solvent is removed, and the residue is dissolved in dichloromethane (20 mL). The resultant is washed with water and saturated aqueous sodium chloride, and then dried with anhydrous magnesium sulfate. After removal of the solvent, the residue is purified by column chromatography (ethyl acetate/petroleum ether=1:6), to afford 0.19 g of pale green solid, y=73.7%.

$^1$H NMR (400 MHz, CDCl$_3$): δ7.30-7.16 (m, 20H, ArH), 5.42-5.41 (brs, 2H, FcH), 4.78-4.79 (t, J=2.4 Hz, 2H, FcH), 4.24-4.08 (m, 4H, OCH$_2$), 3.84-3.83 (brs, 2H, FcH), 1.13-1.10 (s, 6H, CH$_3$).

Example 3

1. Preparation of Amide Ester (3)

(S)-(S)-1,1'-bis(diphenylphosphino)-2,2'-bis[(S)-4-isopropyloxazolinyl]ruthenocene (1.65 g, 2 mmol) is dissolved in tetrahydrofuran (40 mL), into which water (2 mL), trifluoroacetic acid (3.8 mL, 49.4 mmol), and anhydrous sodium sulfate Na$_2$SO$_4$ (18.8 g) are then added successively. The suspension is stirred overnight at the room temperature, followed by filtration and removal of the solvent. The residue is dissolved in dichloromethane (40 mL), into which pyridine (7.2 mL, 89 mmol) and acetic anhydride (12.0 mL, 76.4 mmol) are added successively. After stirring overnight at room temperature, the mixture is diluted with dichloromethane (80 mL), and then washed with dilute hydrochloric acid (10%), water and saturated aqueous sodium chloride, and dried with anhydrous magnesium sulfate. After removal of the solvent, the residue is purified by column chromatography (ethyl acetate) to afford 1.56 g of the target product, y=82.8%.

$^1$H NMR (400 MHz, CDCl$_3$): δ7.34-7.14 (m, 20H, ArH), 6.59-6.58 (brs, 2H, NH), 5.39 (brs, 2H, RcH), 4.83 (brs, 2H, RcH), 4.39-4.34 (dd, J=4 Hz, 15.6, 2H, OCH), 4.05-4.01 (dd, J=3.6 Hz, 11.2 Hz, 2H, OCH), 3.90 (m, 2H, NCH), 3.82 (brs, 2H, FCH), 2.18-2.17 (m, 2H, Me$_2$CH), 2.16 (s, 6H, COCH$_3$), 1.02-1.00 (d, J=8.8 Hz, 6H, CH$_3$), 0.99-0.97 (d, J=8.8 Hz, 6H, CH$_3$).

2. Preparation of (S)-(S)-1,1'-bis(diphenylphosphino)-2,2'-dihydroxymethyl ruthenocene (1)

A solution of amide ester (188 mg, 0.2 mmol) in tetrahydrofuran (2 mL) is added into a suspension of lithium aluminum tetrahydride (46 mg, 6 equiv.) in tetrahydrofuran (8 mL). The mixture is stirred at room temperature for 2-3 hours, and then is quenched carefully with saturated sodium sulfate solution in an ice water bath. Thereafter, the resultant mixture is diluted with ethyl acetate in a volume of three times. The system is washed with 10% solution of hydrochloric acid, saturated aqueous sodium bicarbonate solution, and saturated aqueous sodium chloride successively, and then dried with anhydrous sodium sulfate. After distillation to dryness, the residue is purified by column chromatography (ethyl acetate/petroleum ether=1:4), to afford 110 mg of diol product, y=89.5%.

$^1$H NMR (400 MHz, CDCl$_3$): δ7.43-7.22 (m, 20H, Ar—H), 4.96 (b, 2H, RcH), 4.48 (d, J=12.8 Hz, 2H, —OCH$_2$), 4.23 (b, 2H, RcH), 4.05 (d, J=12.8 Hz, —OCH$_2$), 3.92 (b, 2H, RcH), 3.34 (b, 2H, —OH).

3. Preparation of (S)-(S)-1,1'-bis(diphenylphosphino)-2,2'-bis(methoxymethyl) ruthenocene (1)

The diol (14 mg, 0.022 mmol) is dissolved in DMF (5 mL), into which sodium hydroxide (5 mg, 6 equiv.) and Me$_2$SO$_4$ (8.4 μL) are added. The reaction is carried out at 20~50° C. for 8 h. The system is diluted with dichloromethane, washed with water and saturated aqueous sodium chloride, respectively, and then is dried with anhydrous magnesium sulfate. After removal of the solvent, the residue is purified by column chromatography (ethyl acetate/petroleum ether=1:8), to afford 12.4 mg of the target compound, y=82.0%.

$^1$H NMR (400 MHz, CDCl$_3$): δ7.34-7.22 (m, 20H, Ar—H), 4.83 (b, 2H, RcH), 4.33-4.29 (dd, J=2.8, 11.2 Hz, 2H, —OCH$_2$), 4.25 (b, 2H, RcH), 4.05 (d, J=11.2 Hz, —OCH$_2$), 3.83 (b, 2H, RcH), 3.17 (s, 6H, —OCH$_3$).

Example 4

1. Preparation of Amide Ester (3)

(S)-(S)-1,1'-bis(diphenylphosphino)-2,2'-bis[(S)-4-isopropyloxazolinyl]ruthenocene (1.65 g, 2 mmol) is dissolved in tetrahydrofuran (40 mL), into which water (2 mL), trifluoroacetic acid (3.8 mL, 49.4 mmol), and anhydrous sodium sulfate Na$_2$SO$_4$ (18.8 g) are then added successively. The suspension is stirred overnight at the room temperature, followed by filtration and removal of the solvent. The residue is dissolved in dichloromethane (40 mL), into which pyridine (7.2 mL, 89 mmol) and acetic anhydride (12.0 mL, 76.4 mmol) are added successively. After stirring overnight at room temperature, the mixture is diluted with dichloromethane (80 mL), and then washed with dilute hydrochloric acid (10%), water and saturated aqueous sodium chloride, and dried with anhydrous magnesium sulfate. After removal of the solvent, the residue is purified by column chromatography (ethyl acetate) to afford 1.56 g of the target product, y=82.8%.

$^1$H NMR (400 MHz, CDCl$_3$): δ7.34-7.14 (m, 20H, ArH), 6.59-6.58 (brs, 2H, NH), 5.39 (brs, 2H, RcH), 4.83 (brs, 2H, RcH), 4.39-4.34 (dd, J=4 Hz, 15.6, 2H, OCH), 4.05-4.01 (dd, J=3.6 Hz, 11.2 Hz, 2H, OCH), 3.90 (m, 2H, NCH), 3.82 (brs, 2H, FCH), 2.18-2.17 (m, 2H, Me$_2$CH), 2.16 (s, 6H, COCH$_3$), 1.02-1.00 (d, J=8.8 Hz, 6H, CH$_3$), 0.99-0.97 (d, J=8.8 Hz, 6H, CH$_3$).

2. Preparation of (S)-(S)-1,1'-bis(diphenylphosphino)-2,2'-dihydroxymethyl ruthenocene (1)

A solution of amide ester (188 mg, 0.2 mmol) in tetrahydrofuran (2 mL) is added into a suspension of lithium aluminum tetrahydride (46 mg, 6 equiv.) in tetrahydrofuran (8 mL). The mixture is stirred at room temperature for 2-3 hours, and then is quenched carefully with saturated sodium sulfate solution in an ice water bath. Thereafter, the resultant mixture is diluted with ethyl acetate in a volume of three times. The system is washed with 10% solution of hydrochloric acid, saturated aqueous sodium bicarbonate solution, and saturated aqueous sodium chloride successively, and then dried with anhydrous sodium sulfate. After distillation to dryness, the residue is purified by column chromatography (ethyl acetate/petroleum ether=1:4), to afford 110 mg of diol product, y=89.5%.

$^1$H NMR (400 MHz, CDCl$_3$): δ7.43-7.22 (m, 20H, Ar—H), 4.96 (b, 2H, RcH), 4.48 (d, J=12.8 Hz, 2H, —OCH$_2$), 4.23 (b, 2H, RcH), 4.05 (d, J=12.8 Hz, —OCH$_2$), 3.92 (b, 2H, RcH), 3.34 (b, 2H, —OH).

3. Preparation of (S)-(S)-1,1'-bis(diphenylphosphino)-2,2'-bis(ethoxymethyl) ruthenocene (1)

The diol (33 mg, 0.05 mmol) is dissolved in DMSO (10 mL), into which sodium hydroxide (1 mg, 6 equiv.) and Et$_2$SO$_4$ (14.2 μL, 3 equiv.) are added. The reaction is carried out at 20~50° C. for 8 h. The system is diluted with dichloromethane, washed with water and saturated aqueous sodium chloride, respectively, and then dried with anhydrous magnesium sulfate. After removal of the solvent, the residue is purified by column chromatography (ethyl acetate/petroleum ether=1:8), to afford 27.9 mg of the target compound, y=78%.

$^1$H NMR (400 MHz, CDCl$_3$): δ7.51-7.19 (m, 20H, Ar—H), 4.83 (b, 2H, RcH), 4.35-4.32 (dd, J=11.6, 2 Hz, 2H, RcCH$_2$), 4.26 (b, 2H, RcH), 4.10 (d, J=11.6 Hz, 2H, RcH), 3.82 (b, 2H, RcH), 3.40-3.24 (m, 4H, OCH$_2$), 0.89 (t, J=6.8, 6H, —CH$_3$).

The invention claimed is:

1. A C$_2$-symmetrical ruthenocene diphosphine ligand having only planar chirality, characterized in that, said ligand has the following formula (1a) or (1b):

(1a)

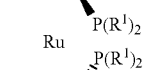

(1b)

wherein, R represents a methyl or ethyl group, and R$^1$ represents a linear or branched alkyl, cycloalkyl, alkoxy, aryl, aralkyl, alkyl amino group.

2. The C$_2$-symmetrical ruthenocene diphosphine ligand having only planar chirality according to claim 1, characterized in that, the planar chirality is a (S,S) configuration.

3. The C$_2$-symmetrical ruthenocene diphosphine ligand having only planar chirality according to claim 1, characterized in that, the R$^1$ in the formula represents a phenyl group.

4. A method for synthesizing a C$_2$-symmetrical ruthenocene diphosphine ligand having only planar chirality, characterized by, synthesizing a C$_2$-symmetrical ruthenocene diphosphine ligand having only planar chirality as shown in the following formula (1a),

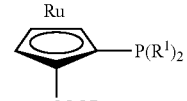

(1a)

in the formula (1a), R represents a methyl or ethyl group, and R$^1$ represents a linear or branched alkyl, cycloalkyl, alkoxy, aryl, aralkyl, alkyl amino group, the method for synthesizing includes:

Step (1): reacting a bisoxazoline compound as shown in the following formula (2) with an acid in a solvent to open the oxazoline ring, and then reacting the thus obtained compound with acetic anhydride to give the corresponding ester amide compound,

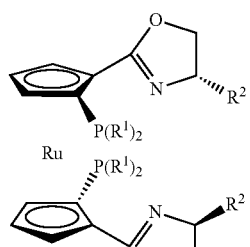

(2)

in the formula (2), R$^1$ is defined as above, and R$^2$ represents an alkyl group;

Step (2A): reacting said ester amide compound with an alkoxide as shown in the following formula:

R-OM wherein R is defined as above, and M represents an alkali metal atom.

5. A method for synthesizing a C$_2$-symmetrical ruthenocene diphosphine ligand having only planar chirality, characterized by, synthesizing a C$_2$-symmetrical ruthenocene diphosphine ligand having only planar chirality as shown in the following formula (1b),

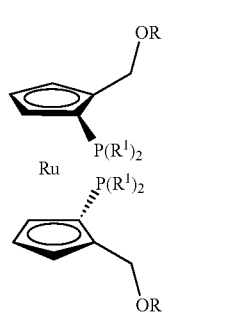

(1b)

in the formula (1b), R represents a methyl or ethyl group, and R$^1$ represents a linear or branched alkyl, cycloalkyl, alkoxy, aryl, aralkyl, alkyl amino group, the method for synthesizing includes:

Step (1): reacting a bisoxazoline compound as shown in the following formula (2) with an acid in a solvent to open the oxazoline ring, and then reacting the thus obtained compound with acetic anhydride to give the corresponding ester amide compound,

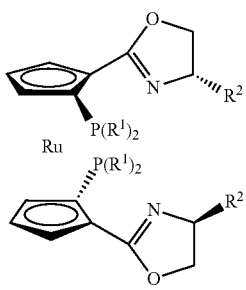 (2)

in the formula (2), $R^1$ is defined as above, and $R^2$ represents an alkyl group;

Step (2B): reacting said ester amide compound with a strong base, and reacting the thus obtained compound with an alkylating agent as shown in the following formula under a basic condition:

$R_2SO_4$ wherein R is defined as above.

6. The method for synthesizing a $C_2$-symmetrical ruthenocene diphosphine ligand having only planar chirality according to claim 4 or 5, characterized in that, in the Step (1), the acid is trifluoroacetic acid.

7. The method for synthesizing a $C_2$-symmetrical ruthenocene diphosphine ligand having only planar chirality according to claim 4 or 5, characterized in that,
in the Step (1), a hydrolyzation is conducted at the presence of trifluoroacetic acid, and the obtained hydrolysis product is reacted with acetic anhydride under a basic condition for acylation.

8. The method for synthesizing a $C_2$-symmetrical ruthenocene diphosphine ligand having only planar chirality according to claim 5, characterized in that,
in the Step (2B) described above, the strong base is lithium aluminum tetrahydride.

9. The $C_2$-symmetrical ruthenocene diphosphine ligand having only planar chirality according to claim 1, wherein said ligand has the formula (1a).

10. The $C_2$-symmetrical ruthenocene diphosphine ligand having only planar chirality according to claim 1, wherein said ligand has the formula (1b).

* * * * *